United States Patent
Large

(10) Patent No.: US 12,296,188 B2
(45) Date of Patent: *May 13, 2025

(54) SYSTEMS AND METHODS FOR COUNTER-PHASE DICHOPTIC STIMULATION

(71) Applicant: OSCILLOSCAPE, LLC, East Hartford, CT (US)

(72) Inventor: Edward W. Large, East Hartford, CT (US)

(73) Assignee: Oscilloscape, LLC, East Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/225,460

(22) Filed: Jul. 24, 2023

(65) Prior Publication Data

US 2024/0335675 A1 Oct. 10, 2024

Related U.S. Application Data

(63) Continuation of application No. 18/132,852, filed on Apr. 10, 2023, now Pat. No. 11,730,975.

(51) Int. Cl.
*A61N 5/06* (2006.01)
(52) U.S. Cl.
CPC .... *A61N 5/0622* (2013.01); *A61N 2005/0627* (2013.01); *A61N 2005/0648* (2013.01)
(58) Field of Classification Search
CPC .......... A61N 5/0622; A61N 2005/0627; A61N 2005/0648
See application file for complete search history.

(56) References Cited

U.S. PATENT DOCUMENTS

| | | | |
|---|---|---|---|
| 6,592,222 B2 | 7/2003 | Massengill et al. | |
| 10,960,225 B2 | 3/2021 | Adaikkan et al. | |
| 11,298,502 B2* | 4/2022 | Hanbury | A61M 21/00 |
| 11,730,975 B1* | 8/2023 | Large | A61N 5/0618 |
| | | | 607/88 |
| 2002/0047987 A1 | 4/2002 | Massengill et al. | |
| 2010/0331912 A1 | 12/2010 | Tass et al. | |
| 2015/0297108 A1 | 10/2015 | Chase et al. | |
| 2019/0082990 A1 | 3/2019 | Poltorak | |
| 2019/0314641 A1 | 10/2019 | Malchano et al. | |
| 2019/0321585 A1* | 10/2019 | Hanbury | A61H 23/0245 |
| 2020/0390997 A1 | 12/2020 | Jovanov | |
| 2021/0236806 A1* | 8/2021 | Simons | A61N 1/36031 |

(Continued)

OTHER PUBLICATIONS

Alais, D., et al., "Binocular rivalry produced by temporal frequency differences," Front. Hum. Neurosci., Jul. 31, 2012, vol. 6, pp. 1-39.

(Continued)

*Primary Examiner* — Jonathan T Kuo
(74) *Attorney, Agent, or Firm* — Foley & Lardner LLP

(57) ABSTRACT

Systems and methods for counter-phased binocular stimulation may include a device that determines a target frequency of a stimulation response. The device may output a first visual stimulation at a first frequency and a first phase to a first eye. The device may output a second visual stimulation at a second frequency and a second phase to a second eye. The first visual stimulation and the second visual stimulation may together produce the stimulation response at the target frequency.

18 Claims, 15 Drawing Sheets

(56) References Cited

U.S. PATENT DOCUMENTS

2021/0339043 A1 11/2021 Malchano et al.
2022/0233879 A1 7/2022 Tsai et al.

OTHER PUBLICATIONS

Aref, A.A., et al., "Frequency Doubling Technology," American Academy of Ophthalmology, Dec. 27, 2021.
Brown, A., et al., "Human Flicker Fusion Correlates with Physiological Measures of Magnocellular Neural Efficiency," Frontiers in Human Neuroscience, May 14, 2018, vol. 12, Article 176, pp. 1-7.
Cavonius, C.R., et al., "Counterphase dichoptic flicker is seen as its own second harmonic," Ophthal. Physiol. Opt., 1992, vol. 12, pp. 153-156.
Notice of Allowance on from U.S. Appl. No. 18/132,852, dated Jun. 16, 2023.
International Search Report and Written Opinion for PCT Application No. PCT/US2024/23671 dated Jul. 25, 2024.

\* cited by examiner

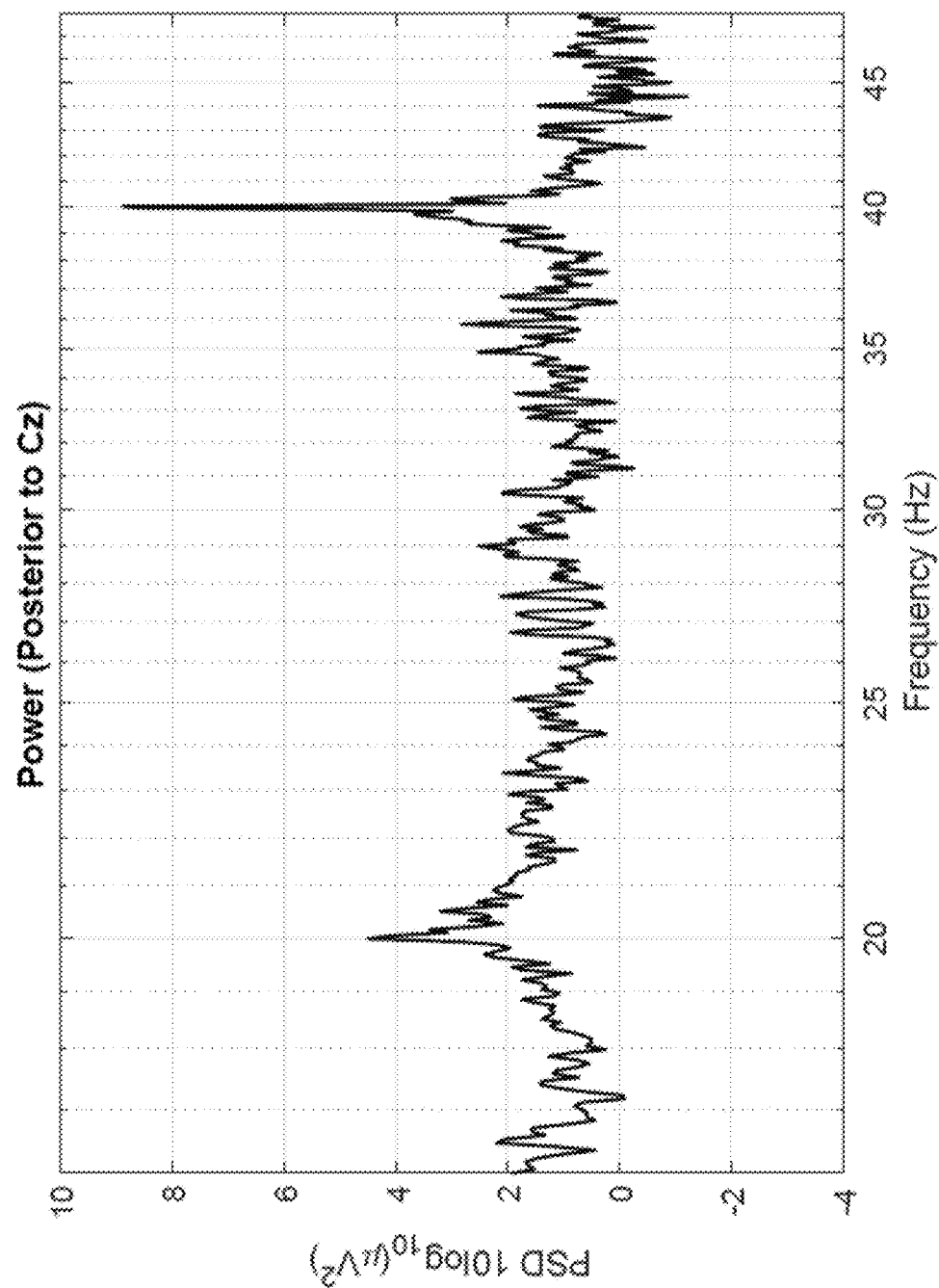

SYSTEMS AND METHODS FOR COUNTER-PHASE DICHOPTIC STIMULATION

CROSS-REFERENCE TO RELATED APPLICATIONS

This application is a continuation of U.S. patent application Ser. No. 18/132,852, filed Apr. 10, 2023, the contents of which are incorporated herein by reference in their entirety.

FIELD OF DISCLOSURE

The present disclosure is generally related to neural stimulation.

BACKGROUND

Neural oscillation occurs in humans and animals and includes rhythmic or repetitive neural activity in the central nervous system. Neural tissue can generate oscillatory activity by mechanisms within individual neurons or by interactions between neurons. Oscillations can appear as either periodic fluctuations in membrane potential or as rhythmic patterns of action potentials, which can produce oscillatory activation of post-synaptic neurons. Synchronized activity of a group of neurons can give rise to macroscopic oscillations, which can be observed by sensing electrical or magnetic fields in the brain using techniques such as electroencephalography (EEG), intracranial EEG (iEEG), also known as electrocorticography (ECoG), and magnetoencephalography (MEG).

SUMMARY

According to the systems and methods described herein, neural stimulation can be provided via counter-phased or interleaved dichoptic (e.g., binocular) stimulation in which a separate field or stimulus is presented to or provided to each eye. The systems and methods described herein may produce or provide stimulation at a target frequency, using counter-phased dichoptic (or binocular) stimulation at frequencies which are less than the target frequency. Some systems, to provide stimulation at a target frequency, will simply output the stimulation at the target frequency. For example, to provide stimulation at a target frequency of 40 Hz, some systems will output stimulation at 40 Hz. As opposed to such systems, it has been observed that providing counter-phased or interleaved binocular stimulation at reduced frequencies (such as half-target frequencies) produces a greater stimulation response at the target frequency as compared to providing stimulus at the target frequency, depending on the target frequency and other parameters of the stimulus. The stimulation can adjust, control or otherwise affect the frequency of the neural oscillations to provide beneficial effects to one or more cognitive states, cognitive functions, the immune system or inflammation, while mitigating or preventing adverse consequences on a cognitive state or cognitive function. For example, stimulation responses to the systems and methods of the present technology can treat, prevent, protect against or otherwise affect Alzheimer's Disease or other cognitive or neurological disorders.

In various instances, where a patient is undergoing treatment or is otherwise undergoing audio or visual stimulation as described herein, often times that stimulation is at a targeted or particular frequency or frequency band (e.g., in the delta, theta, and/or gamma band) to stimulate a particular response in the patient's brain (e.g., at a particular frequency and/or in particular portions, regions, or areas of the patient's brain). As described below, rather than producing a stimulation at the targeted or particular frequency, the systems and methods described herein may provide a counter-phased stimulation at related or reduced frequencies which provide a combined effect of stimulating the brain at the target frequency, due to non-linear responses of neurons and networks in the brain. Such implementations and embodiments may result in greater stimulation responses in a patient's brain at the target frequency, which may thereby increase the efficacy of treatment.

In one aspect, this disclosure is directed to a method. The method includes determining, by a device, a target frequency of a stimulation response. The method includes outputting, by the device, a first visual stimulation at a first frequency and a first phase to a first eye. The method includes outputting, by the device, a second visual stimulation at a second frequency and a second phase to a second eye. The first visual stimulation and the second visual stimulation may together produce the stimulation response at the target frequency.

In some embodiments, the first frequency is half of the target frequency, and the second frequency is half of the target frequency. In some embodiments, the second phase is anti-phase to the first phase. In some embodiments, the target frequency is between 35 and 40 Hz. In some embodiments, a sum of the first frequency and the second frequency is equal to the target frequency. In some embodiments, the target frequency is equal to 38 Hz, the first frequency is equal to 19 Hz, and the second frequency is equal to 19 Hz.

In some embodiments, the device includes one or more first light sources for stimulating the first eye, and one or more second light sources for stimulating the second eye. Outputting the first visual stimulation may include controlling the one or more first light sources to output light at the first frequency and the first phase. Outputting the second visual stimulation may include controlling the one or more second light sources to output light at the second frequency and the second phase. In some embodiments, the device includes a head-wearable device having the one or more first light sources located at a first position of the head-wearable device and the one or more second light sources located at a second position of the head-wearable device. The first position may correspond to stimulating the first eye when the head-wearable device is worn, and the second position may correspond to stimulating the second eye when the head-wearable device is worn.

In another aspect, this disclosure is directed to a device. The device includes one or more light sources. The device includes one or more processors configured to determine a target frequency of a stimulation response, output a first visual stimulation at a first frequency and a first phase to a first eye, and output a second visual stimulation at a second frequency and a second phase to a second eye. The first visual stimulation and the second visual stimulation may together produce the stimulation response at the target frequency.

In some embodiments, the first frequency is half of the target frequency, the second frequency is half of the target frequency, and the second phase is anti-phase to the first phase. In some embodiments, the target frequency is equal to 38 Hz, the first frequency is equal to 19 Hz, and the second frequency is equal to 19 Hz.

In yet another aspect, this disclosure is directed to a system. The system includes one or more light sources. The system includes one or more processors configured to determine a target frequency of a stimulation response, output a first visual stimulation at a first frequency and a first phase to a first eye, and output a second visual stimulation at a second frequency and a second phase to a second eye. The first visual stimulation and the second visual stimulation may together produce the stimulation response at the target frequency.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing.

FIG. 8A-FIG. 8F depicts a series of graphs illustrating a power spectral density and gain for the different types of input stimulus shown in FIG. 6 and FIG. 7, according to an example implementation of the present disclosure.

DETAILED DESCRIPTION

Figure 1:
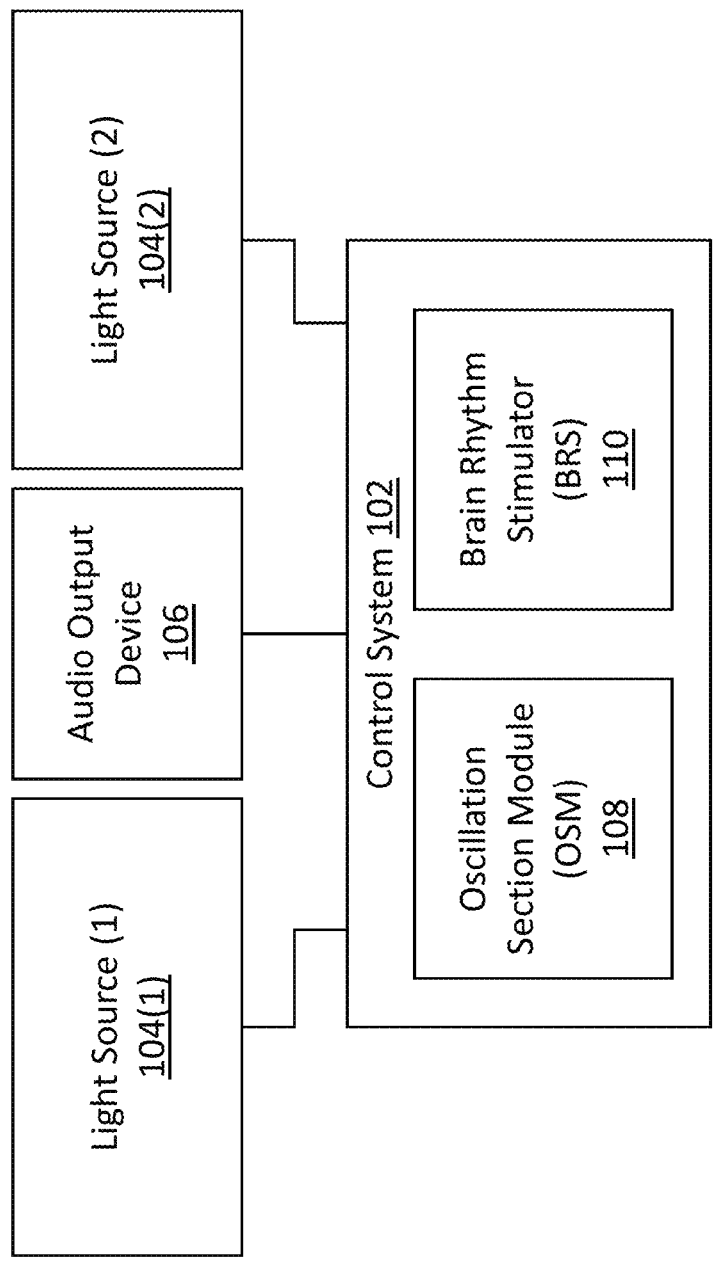
FIG. 1 is a block diagram of a system for counter-phased binocular stimulation, according to an example implementation of the present disclosure.

Before turning to the figures, which illustrate certain embodiments in detail, it should be understood that the present disclosure is not limited to the details or methodology set forth in the description or illustrated in the figures. It should also be understood that the terminology used herein is for the purpose of description only and should not be regarded as limiting.

According to the systems and methods described herein, neural stimulation can be provided via counter-phased (or anti-phased, interleaved, etc.) dichoptic (or binocular) stimulation. The systems and methods described herein may produce or provide stimulation at a target frequency, using counter-phased binocular stimulation at frequencies which are different from (e.g., less than or greater than) the target frequency. Some systems, to provide stimulation at a target frequency, will simply output the stimulation at the target frequency. For example, to provide stimulation at a target frequency of 40 Hz, some systems will output stimulation at 40 Hz. As opposed to such systems, it has been observed that providing counter-phased binocular or dichoptic stimulation at related frequencies (such as half-target frequencies) may produce a greater constructive stimulation response at the target frequency (e.g., when the dichoptic stimulation is constructive or combined) as compared to providing stimulation at the target frequency, for example, when the target frequency is near a flicker fusion threshold. The stimulation can adjust, control or otherwise affect the frequency of the neural oscillations to provide beneficial effects to one or more cognitive states, cognitive functions, the immune system or inflammation, while mitigating or preventing adverse consequences on a cognitive state or cognitive function. For example, stimulation responses to the systems and methods of the present technology can treat, prevent, protect against or otherwise affect Alzheimer's Disease or other cognitive diseases.

In various instances, where a patient is undergoing treatment or is otherwise undergoing audio stimulation as described herein, often times that stimulation is at a targeted or particular frequency or frequency band (e.g., in the delta, theta, and/or gamma band) to stimulate a response in the patient's brain and/or a particular portion of the patient's brain. As described below, rather than producing a stimulation at the targeted or particular frequency as may be performed by some systems or solutions, the systems and methods described herein may provide a stimulation at related frequencies which provide a combined effect of stimulation responses at the target frequency due to non-linear responses of neurons and networks in the brain. Such implementations and embodiments may result in greater stimulation responses in a patient's brain at the target frequency, which may thereby increase the efficacy of treatment.

Neural oscillations can be characterized by their frequency, amplitude, and phase. These signal properties can be observed from neural recordings using time-frequency analyses. For example, an EEG can measure oscillatory activity among a group of neurons, and the measured oscillatory activity can be categorized into frequency bands as follows: delta activity corresponds to a frequency band from 0.5-4 Hz; theta activity corresponds to a frequency band from 4-8 Hz, alpha activity corresponds to a frequency band from 8-13 Hz; beta activity corresponds to a frequency band from 13-30 Hz; and gamma activity corresponds to a frequency band of 30 Hz and above.

Neural oscillations of different frequency bands can be associated with cognitive states or cognitive functions such as perception, action, attention, reward, learning, and memory. Based on the cognitive state or cognitive function, the neural oscillations in one or more frequency bands may be involved. Further, neural oscillations in one or more frequency bands can have beneficial effects or adverse consequences on one or more cognitive states or functions.

Neural entrainment occurs when an external stimulation of a particular frequency or combination of frequencies is perceived by the brain and triggers neural activity in the brain that results in neurons oscillating at frequencies related to the particular frequencies of the external stimulation. Thus, neural entrainment can refer to synchronizing neural oscillations in the brain using external stimulation such that the neural oscillations occur at the frequencies corresponding to the particular frequencies of the external stimulation.

Neural entrainment can also refer to synchronizing neural oscillations in the brain using external stimulation such that the neural oscillations occur at frequencies that correspond to harmonics, subharmonics, integer ratios, and combinations of the particular frequencies of the external stimulation. The specific neural oscillatory frequencies can be observed in response to a set of external stimulation frequencies. The neural oscillatory frequencies can be caused by nonlinear responses of neurons and networks in the brain, and can be predicted by models of neural oscillation and neural entrainment. The models may be based in part on Equation 1 below, which describes how stimulus frequencies may be related to the target response frequency:

$$m\omega_{response} = k_1\omega_{stim1} + k_2\omega_{stim2} + \ldots + k_N\omega_{stimN} \quad \text{Eq. 1}$$

where, m and k are equal to positive (or negative) integers, $\omega_{response}$ is equal to the response frequency, and $\omega_{stim1}$ through $\omega_{stimN}$ are equal to the stimulus frequencies.

Cognitive functions such as learning and memory involve coordinated activity across distributed subcortical and cortical brain regions, including hippocampus, cortical and subcortical association areas, sensory regions, and prefrontal cortex. Across different brain regions, behaviorally relevant information is encoded, maintained, and retrieved through transient increases in the power of and synchronization between neural oscillations that reflect multiple frequencies of activity.

In particular, oscillatory neural activity in the theta and gamma frequency bands are associated with encoding, maintenance, and retrieval processes during short-term, working, and long-term memory. Induced gamma activity has been implicated in working memory, with increases in scalp-recorded and intracranial gamma-band activity occurring during working-memory maintenance. Increases in the power of gamma activity dynamically track the number of items maintained in working memory. Using electrocorticography (ECoG), one study found enhancements in gamma power tracked working-memory load in the hippocampus and medial temporal lobe, as participants maintained sequences of letters or faces in working memory. Finally, other evidence indicates that hippocampal gamma activity aids episodic memory, with distinct sub-gamma frequency bands corresponding to encoding and retrieval stages.

Theta oscillations (4-8 Hz) have been linked to working and episodic memory processes. Intracranial EEG (iEEG) recordings demonstrate that, during working memory, theta oscillations gate on and off (i.e., increase and sustain in amplitude, before rapidly decreasing in amplitude) over the encoding, maintenance, and retrieval stages. Other work has observed increases in scalp-recorded theta activity during working-memory maintenance. Some studies have concluded that scalp-recorded theta activity, emerging from frontal-midline electrodes, was the most robust neural correlation of verbal working-memory maintenance. Moreover, frontal-midline theta activity tracks working-memory load, increasing and sustaining in power as a function of the number of items maintained in working memory.

Some studies have found that gamma-frequency, auditory-visual stimulation can ameliorate dementia or Alzheimer's Disease (AD)-related biomarkers and pathophysiologies, and, if administered during an early stage of disease progression, can provide neuroprotection. The systems and methods described herein may produce or provide frequency responses or oscillatory neural activity at various target frequencies, as described in greater detail below. Such responses or oscillatory neural activity may provide treatment or otherwise improve the impact of various cognitive diseases, such as any one of those set forth herein (or any other cognitive disease).

Referring to FIG. 1, depicted is a block diagram of a system 100 for counter-phased binocular stimulation, according to an example implementation of the present disclosure. The system 100 may include a control system 102 communicably coupled to a plurality of light sources 104 (e.g., first light source 104(1) and second light source 104(2) and an audio output device 106. The control system 102 may include an oscillation selection module (OSM) 108 and a brain rhythm stimulator (BRS) 110. As described in greater detail below, the control system 102 may be configured to determine to output visual stimulation at a target frequency. The control system 102 may be configured to output a first visual stimulation at a first frequency and phase to a first eye (e.g., via the first light source 104(1)) and output a second visual stimulation at a second frequency and phase to a second eye (e.g., via the second light source 104(2)).

The control system 102 may include an Oscillation Selection Module (OSM) 108. The OSM 310 may be communicably coupled to various other components or elements of the control system 102 (such as various input/output devices, user interface devices, user profiles, processing components, or other components/elements/devices/hardware of the system, such as those described in greater detail below). The OSM 310 may be configured to determine, select, or otherwise identify various oscillation states for stimulating a patient. The oscillation states may be or include a target frequency and various sub-oscillation states for providing or achieving stimulation at the target frequency.

The OSM 108 may be configured to receive, detect, identify, or otherwise determine to output visual stimulation at a target frequency. The target frequency may be or include a frequency which is within a frequency band (such as the delta, theta, and/or gamma frequency ranges or bands). In some embodiments, the OSM 108 may be configured to receive a user input (e.g., from the patient, from a treating professional associated with the patient, etc.) which specifies, selects, or otherwise identifies the target frequency. In some embodiments, the OSM 108 may be configured to identify the target frequency based on a setting in a profile for the patient (e.g., a treatment plan defining or setting a schedule of a certain target frequency at certain times of day). In some embodiments, the OSM 108 may be configured to identify the target frequency based on or according to a simulated response to a given frequency (e.g., a simulated brain response to different input frequencies). For example, the OSM 108 may be configured to select the target frequency from the input frequencies based on which of the input frequencies results in the strongest simulated brain response.

The OSM 108 may be configured to determine, detect, or otherwise identify an oscillation state to provide the target frequency. An oscillation state may be defined as or include a frequency, amplitude, and phase of visual stimulation which produces a corresponding frequency. In some embodiments, the OSM 108 may be configured to determine, select, or otherwise define the oscillation states to provide the stimulation response at the target frequency. The frequency of the oscillation state may be less than the target frequency. The OSM 108 may be configured to define the oscillation state for stimulation provided to each of the patient's eyes. The OSM 108 may be configured to define a first oscillation state for providing visual stimulation to one of the patient's eyes, and define a second oscillation state for providing visual stimulation to the other one of the patient's eyes. The OSM 108 may be configured to define the oscillation states to specify a respective frequency, amplitude, and phase, to produce a stimulation response at the target frequency. In this regard, the OSM 108 may be configured to select, determine, or otherwise define different oscillation states for respective eyes, to produce a stimulation response in the patient's brain based on a combined effect of the different oscillation states.

Figure 2:
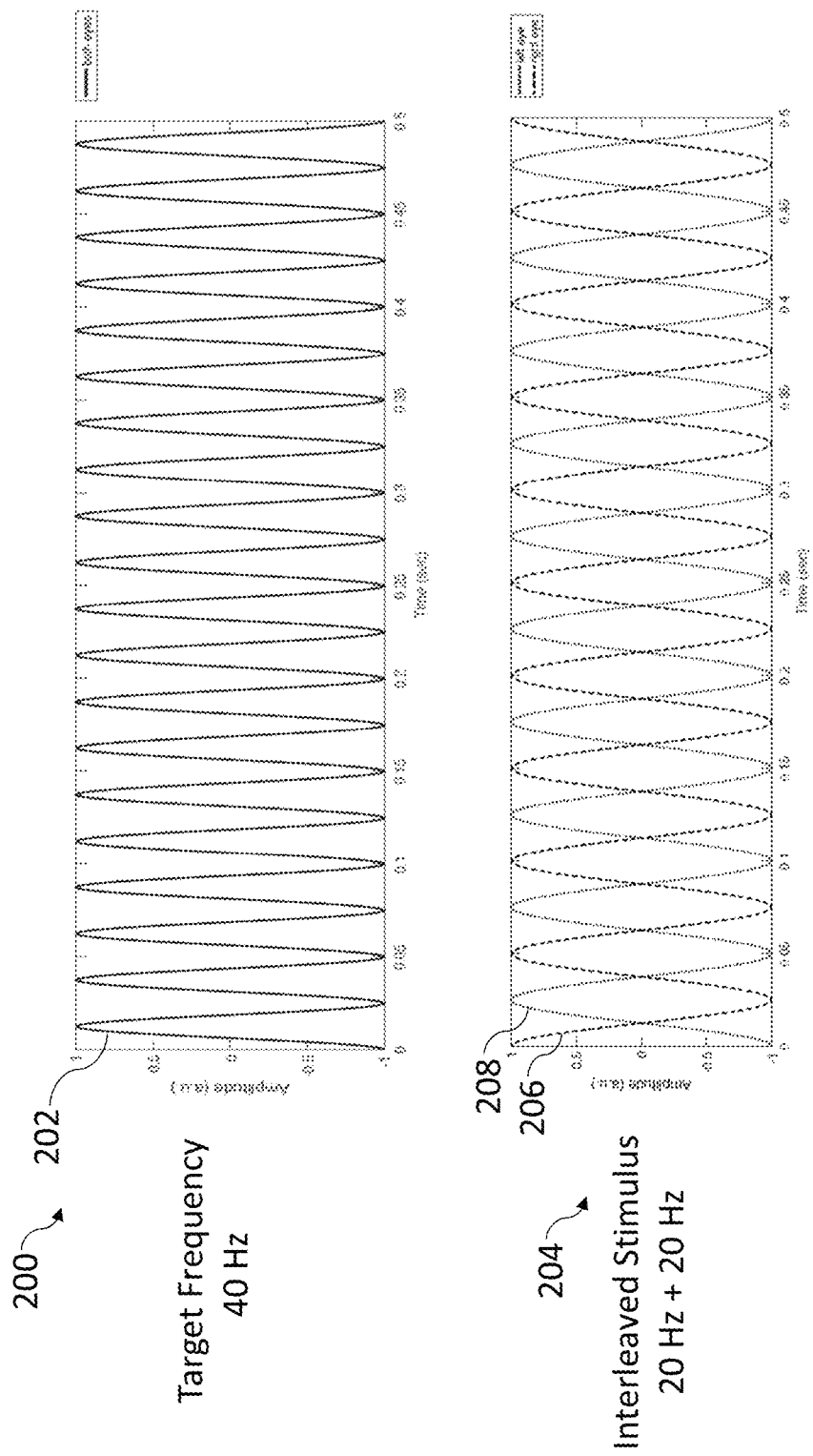
FIG. 2 depicts a first graph showing a target frequency and a second graph showing the oscillation states to provide the target frequency, according to an example implementation of the present disclosure.

Referring now to FIG. 1 together with FIG. 2, the OSM 108 may be configured to define or set oscillation states to provide the target frequency response. Specifically, FIG. 2 depicts a first graph 200 showing a target frequency 202 and a second graph 204 showing the oscillation states 206, 208 of stimulation waveforms that provide a stimulation response at target frequency. As shown, the oscillation states 206, 208 may include one oscillation state for one stimulation waveform provided to one eye and another oscillation state for another stimulation waveform provided to another eye. The target frequency illustrated in FIG. 2 is 40 Hz, though it is noted that the systems and methods described herein may be used for multiple frequencies in the various frequency bands. For example, the target frequency may be 40 Hz as illustrated, between 30-40 Hz (such as between 35-40 Hz, or 38 Hz), between 13-30 Hz, between 8-13 Hz, between 4-8 Hz, between 0.5-4 Hz, or greater than 40 Hz.

As illustrated in FIG. 2, the OSM 108 may be configured to determine an oscillation state for a first visual stimulation and an oscillation state for a second visual stimulation which is different from the first visual stimulation, based on or according to the intended or target stimulation. The OSM 108 may be configured to determine the oscillation states by selecting (e.g., for each oscillation state) the frequency, amplitude, and phase according to the target frequency. The OSM 108 may be configured to determine the phase of the oscillation states such that oscillation states are out of phase (or counterphased) from one another. The OSM 108 may be configured to determine the phase such that the oscillation state for the first visual stimulation is counterphased/interleaved/opposite to the oscillation state for the second visual stimulation. As illustrated in FIG. 2, while the oscillation state 206 for the first visual stimulation and the oscillation state 208 for the second visual stimulation may have the same frequency, the corresponding signals may be counterphased/interleaved with/opposite to one another, thereby producing a combined effect which is constructive.

In some embodiments, the OSM 108 may be configured to determine the frequency and amplitude for each oscillation state based on or according to the target frequency. The OSM 108 may be configured to determine the frequencies and amplitudes such that, when combined, the stimulation response is at the target frequency. As such, the frequency for each oscillation state may be less than the target frequency. The frequency for each oscillation state may be half the target frequency. For example, the OSM 108 may be configured to determine the frequency for one oscillation state as being equal to half the target frequency, and determine the frequency for the other oscillation state as being equal to half the target frequency. Where the target frequency is between 35-40 Hz, for example, the OSM 108 may be configured to determine the frequency for each oscillation state to be equal to between 17.5-20 Hz.

The control system 102 may include a brain rhythm stimulator (BRS) 110. The BRS 110 may be configured to generate, produce, or otherwise provide a control signal for an output device (e.g., the light sources 104 and/or audio output device 106), to provide audio and/or visual stimulation, based on the oscillation states determined by the OSM 108. The BRS 110 may be configured to use the oscillation states to produce or provide visual stimulation in or at the selected frequency (or frequency ranges) via one or more output devices (e.g., the light source(s) 104, audio output device 106, etc.). In some embodiments, the BRS 110 may output rhythmic visual stimulation to the user. The BRS 110 can include a pattern buffer, a generation module, adjustment module, and a filtering component, and may be operatively connected to an output device for outputting the stimulation to the patient.

In some embodiments, the OSM 108 and BRS 110 may be configured to determine, identify, or otherwise provide an audio signal for synchronization with the visual stimulation. For example, the control system 102 may be configured to pre-process an auditory stimulus, auditory input, or audio signal, to provide multi-channel rhythmic inputs (e.g., note onsets). In some embodiments, the auditory input or audio signal is provided by the control system 102, such as by or via a built-in audio playback system that has access to a library of songs and/or other musical compositions. In some embodiments, the system 102 may further comprise a graphical display and input/output accessible to the user (e.g. patient or therapist) to allow the user to make a selection from the library for playback. In other embodiments, in addition to or as an alternative to a built-in audio playback system, the control system 102 may include an auxiliary audio input to allow the system to receive input from a secondary playback system, such as a personal music playback device (e.g. an iPod, MP3 player, smart phone, or the like). In some embodiments, in addition to or as an alternative to the above auditory input, the system 102 may include a microphone or similar device to allow the system 102 to receive auditory input from ambient sound, such as a live musical performance or music broadcast from secondary speakers, such as the user's home stereo system. In embodiments where the audio signal is received by the system through a built-in playback system or auxiliary input such as through a MP3 player, the system may further comprise headphones or integrated speakers to allow the listener to hear the audio signal 102 in real time.

The OSM 108 may be configured to select the most prominent oscillations from the audio signal for configuring, selecting, or otherwise determining an oscillation state for visual stimulation synchronized to the audio stimulation. In some embodiments, the OSM 108 may couple the visual frequency stimulation to the beat and rhythmic structure of music. The OSM 108 may select variable, music-based frequencies in the delta, theta and gamma ranges for visual stimulation to the user, synchronized to the audio stimulation described herein. In some embodiments, the OSM 108 may modulate the visual signal at certain frequencies to produce a visual stimulation synchronized to the audio signal. For example, the OSM 108 may amplitude modulate a beta or gamma frequency visual signal at theta frequencies (and/or at various other frequencies, such as delta frequencies) that are derived from or determined from the musical rhythm. The BRS 110 may be configured to generate, produce, or otherwise provide a control signal for an output device (e.g., the light source 104 and/or audio output device 106 of FIG. 1), to provide audio and/or visual stimulation, based on data from the OSM 108. In some embodiments, the BRS 110 may be configured to use simulated neural oscillations to synchronize visual stimulation in the selected frequency ranges to the rhythm of music via the output device (e.g., the audio output device 106). In some embodiments, the BRS 110 can also interface with a profile manager which stores data pertaining to one or more users or patients. Thus, in some embodiments, information stored by the profile manager may also include previously-captured or user-selected preferences of patterns, waveforms or other parameters of stimulation, such as colors, preferred by the user/patient.

Figure 3:
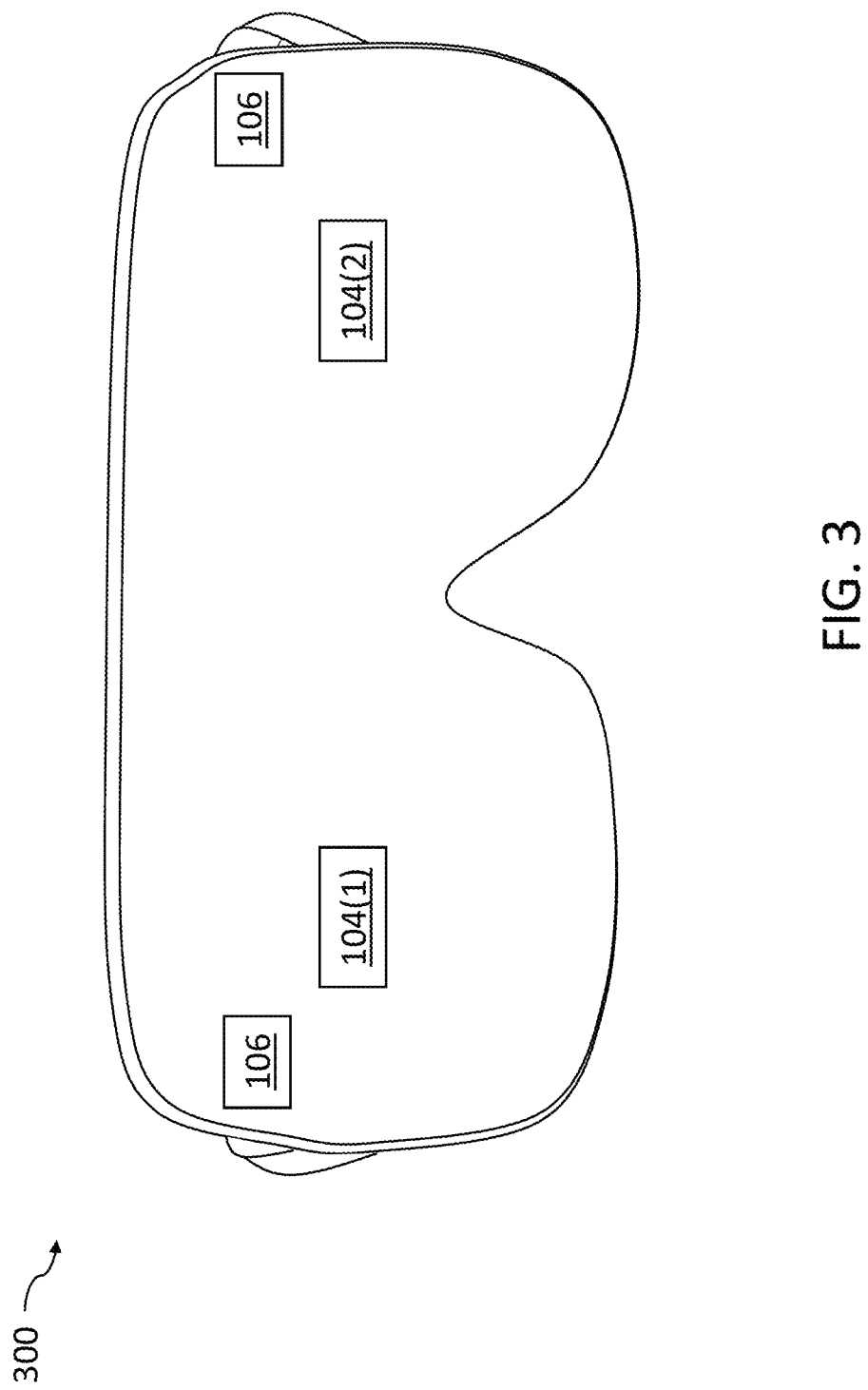
FIG. 3 depicts an example of a head-wearable device for providing visual stimulation, according to an example implementation of the present disclosure.
Figure 4:
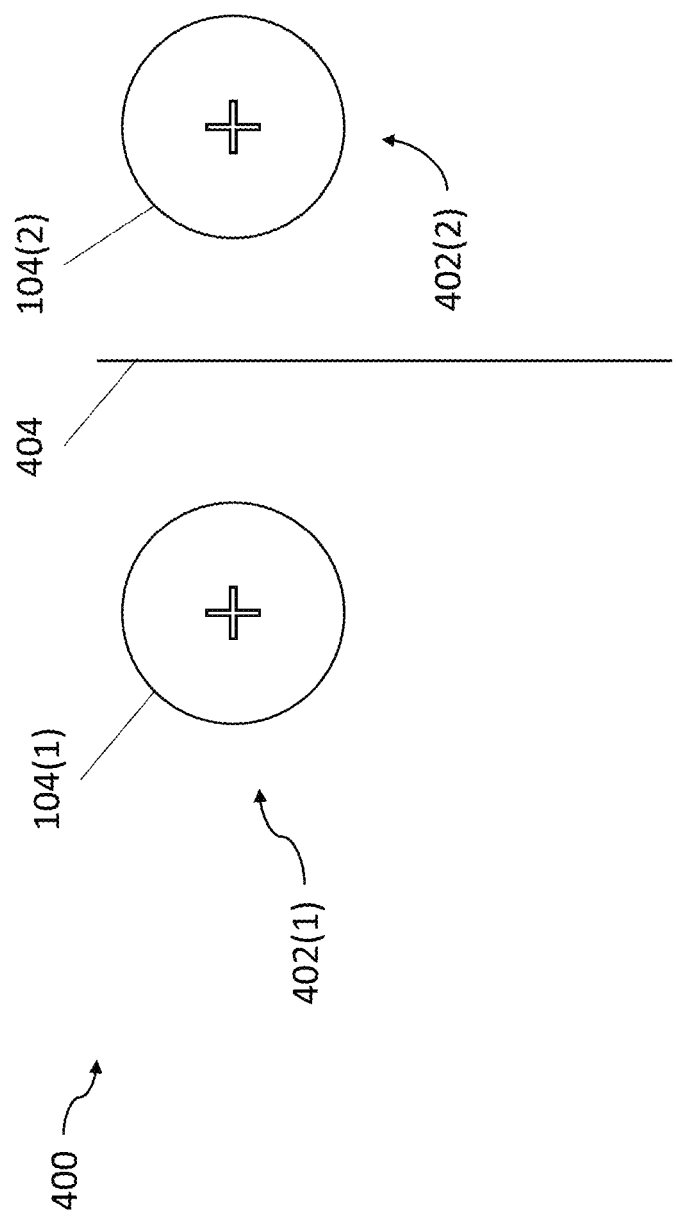
FIG. 4 depicts an example of a system for providing visual stimulation, according to an example implementation of the present disclosure.
Figure 5:
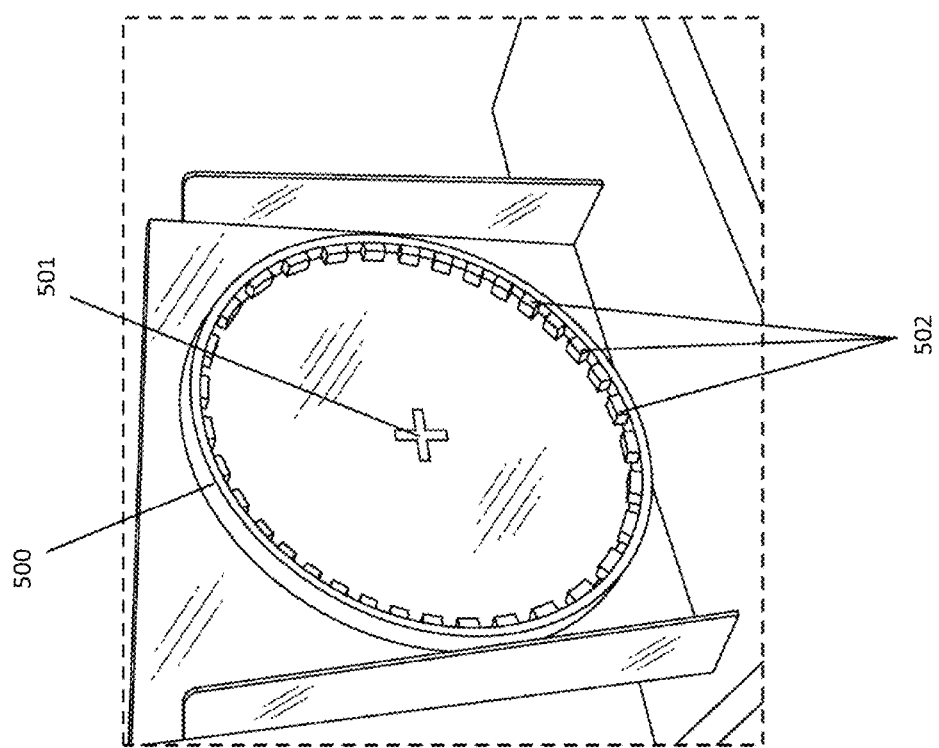
FIG. 5 depicts a lighting system that may be implemented in the system of FIG. 4, according to an example implementation of the present disclosure.

Referring now to FIGS. 3-5, depicted are examples of output devices for providing visual stimulation, according to example implementations of the present disclosure. Specifically, FIG. 3 depicts an example of a head-wearable device 300 for providing visual stimulation, FIG. 4 depicts an example of a system 400 for providing visual stimulation, and FIG. 5 depicts a lighting system 402 of the system 400 of FIG. 4, respectively, according to example implementations of the present disclosure. The output devices may be communicably coupled to the control system 102 described above. In some embodiments, the control system 102 may be embodied on or incorporated into the output devices. For example, the control system 102 may reside on the head-wearable device 300 and communicate with the light source(s) 104(1), 104(2) and/or audio output device 106 to deliver the audio/visual stimulation to the patient locally. In some embodiments, the control system 102 may be remotely located and communicably coupled (e.g., wirelessly) to the output devices. For example, the control system 102 may reside on a cloud-based server, a computing device (e.g., remote or local device), and so forth, and deliver wireless signals to the light sources 104 and/or audio output device 106.

Referring specifically to FIG. 3, the output device used to provide audio/visual stimulation may include a head-wearable device. The head-wearable device may include augmented reality glasses, virtual reality goggles, etc. The display of the head-wearable device may render the visual pattern to the user. For instance, where the head-wearable device includes augmented reality glasses, the augmented reality glasses may augment the environment of the user visible through the glasses with the visual pattern. As another example, where the head-wearable device includes virtual reality goggles (or other non-AR goggles), the goggles may display the visual pattern on displays adjacent to the patient's eyes. In some embodiments, the display of the head-wearable device may display separate visual patterns on each eye of the patient, and at different angles, to provide visual stimulation to the patient.

The head-wearable device 300 may include the light sources 104(1), 104(2) for delivering light to each of the respective eyes of the patient. The light sources 104 may be light sources corresponding to various display (or display devices) of the head-wearable device 300. For example, a display device may include a plurality of light sources, where at least some of the light source(s) are used for delivering light to each of the respective eyes of the patient. The head-wearable device 300 may include a light source 104 for each eye. For example, one light source 104(1) may be dedicated to a particular eye (e.g., the first light source 104(1) may be dedicated to a right eye of the patient, and the second light source 104(2) may be dedicated to a left eye of the patient). The light sources 104 may be arranged on or along an interior-facing portion of the head-wearable device 300, to deliver, direct, or otherwise output light towards and/or at an eye of the patient (when the head-wearable device 300 is worn by the patient). The light source(s) 104 may in some embodiments include light emitting diode(s) LEDs or other types or forms of lights. The light source(s) 104 may be configured or capable of outputting lights in various colors/brightnesses/rhythmic frequencies/etc.

The head-wearable device 300 may include one or more audio output devices 106. In some embodiments, the head-wearable device 300 may include a single audio output device 106 arranged to produce or output an audio signal perceptible by both ears. For example, the audio output device 106 may include a speaker or speaker system. In some embodiments, the head-wearable device 300 may include multiple audio output devices 106 arranged at various locations of the head wearable device 300. For example, the head-wearable device 300 may include ear buds, localized speakers, etc. arranged to produce or output respective audio signals which are perceptible by one of the patient's ears (e.g., a left speaker or ear bud for a left ear, and a right speaker or ear bud for a right ear).

Referring specifically to FIG. 4 and FIG. 5, the output device used to provide audio/visual stimulation may include an audio/visual system 400 including separate light system 402(1), 402(2), according to an example implementation of the present disclosure. The lighting systems 402 may be or include a visual stimulation ring 500 as illustrated in FIG. 5, where the visual stimulation ring includes a plurality of LED lights 702 that are operatively connected to the system 100. In some embodiments, as illustrated in FIG. 4, the system 400 may include dedicated light systems 400 (or visual stimulation rings 500) for each eye of the patient. For example, the lighting systems 402(1), 402(2) may be positioned in front of (e.g., at respective sides of) the participant or patient. The patient may focus on a center of the respective lighting systems 402 (denoted by cross 501 in FIG. 5). To receive counterphased stimulation, the patient may be asked to focus between the center of the respective lighting systems (e.g., illustrated as median 404 in FIG. 4). In some embodiments, the lighting systems 402 may be placed at the appropriate distance to stimulate the retina at a specific visual angle. For example, the lighting systems 402 may be placed at the appropriate distance to stimulate the retina at a visual angle of between 0 and 15 degrees, or between 10 and 60 degrees, or between 15 and 50 degrees, or between 15 and 25 degrees, or between 18 and 22 degrees, or between 19 and 21 degrees. In some embodiments, the lighting systems 402 may be placed at the appropriate distance to stimulate the retina at a visual angle of 20 degrees where the maximum density of rods is found in the retina.

While illustrated as a stimulation ring 500, various other output devices may be used as part of the system 100, either together with the stimulation ring 500 or to supplement the stimulation ring 700. For example, and in some embodiments, the visual systems 402 may include separate displays, a single wide display having dedicated portions for the patient's left and right eyes, and so forth.

Figure 6:
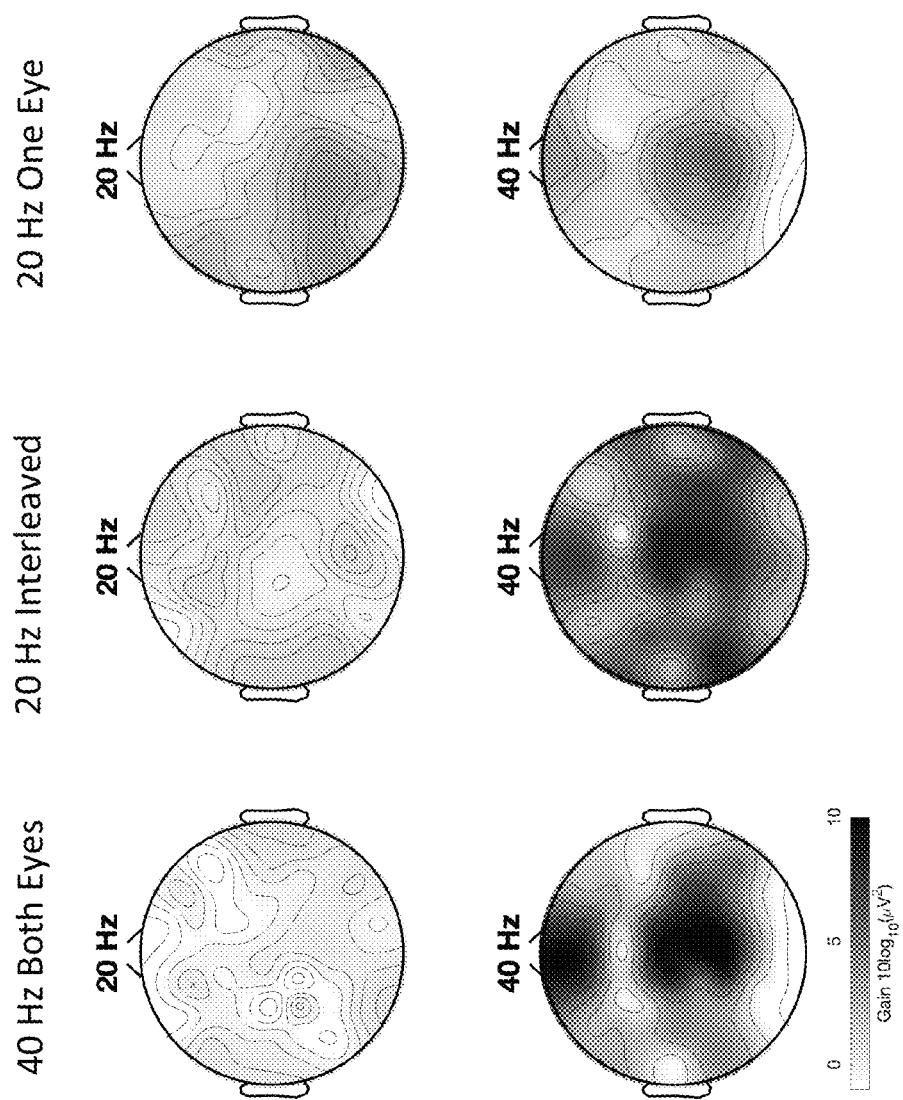
FIG. 6 depicts a series of images illustrating (actual) measured stimulation responses according to different visual stimulation inputs in a patient, according to an example implementation of the present disclosure.
Figure 7:
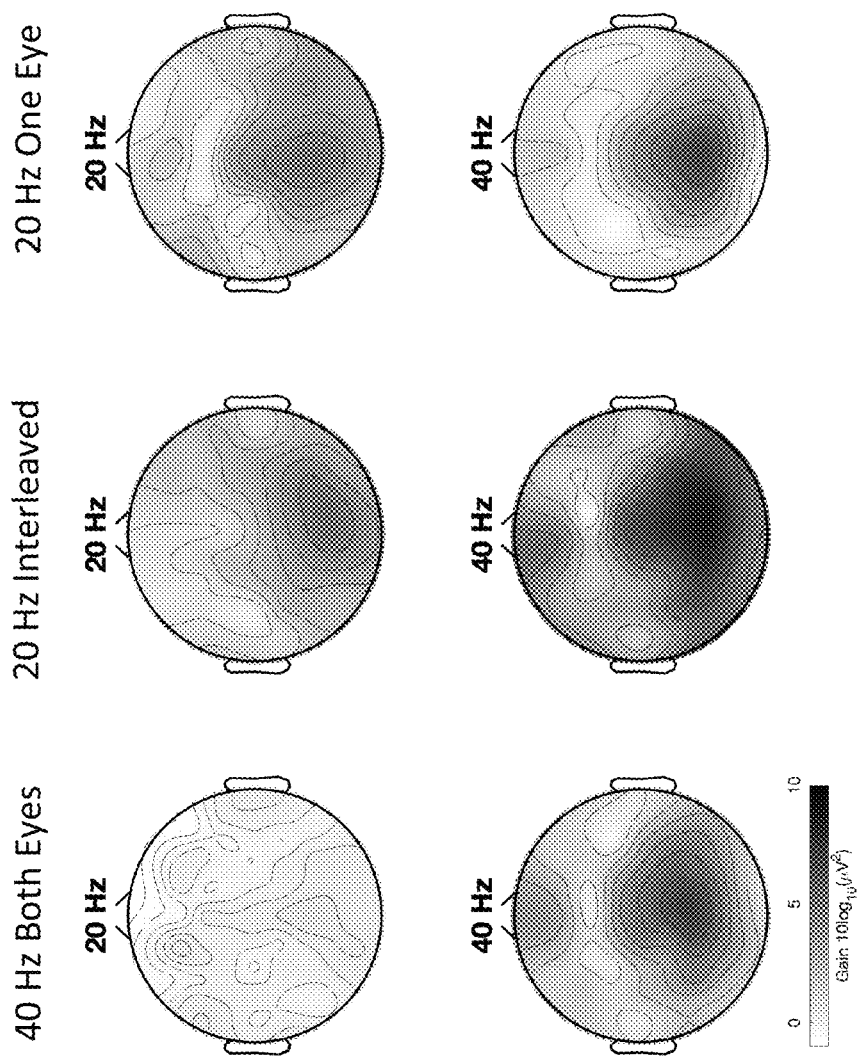
FIG. 7 depicts another series of images illustrating an average stimulation response across a plurality of patients according to different visual stimulation inputs, according to an example implementation of the present disclosure.

Referring now to FIG. 6 and FIG. 7, depicted is a series of images illustrating (actual) measured stimulation responses according to different visual stimulation inputs in a patient, and another series of images illustrating an average stimulation response across a plurality of patients according to different visual stimulation inputs, respectively. In the left-most column, depicted is a measured stimulation response at 20 Hz and 40 Hz, respectively, based on an input visual stimulation of 40 Hz on both eyes. As shown, at 20 Hz, the measured response gain (in dB, e.g., $10 \log_{10} (\mu V^2)$) across the brain of the patient was near zero. At 40 Hz, the measured stimulation response across the brain of the patient was strong in many portions [e.g., frontal and rear portion] of the patient's brain.

In the center column, depicted is the measured stimulation response at 20 Hz and 40 Hz, respectively, based on an input visual stimulation of counterphased (or anti-phased or interleaved) dichoptic stimulation at 20 Hz. As illustrated in the center column, the interleaved dichoptic input stimulation produced a stronger response at 40 Hz across the brain, when compared to the stimulation response to a 40 Hz input stimulation. Additionally, and as shown in the right column, applying a 20 Hz stimulation to one eye (e.g., the stimulation response to 20 Hz applied to the right eye is depicted) produced a weak stimulation response at the 40 Hz harmonic, due to nonlinear responses of neurons and networks in the brain. However, the 40 Hz response to the interleaved stimulus (middle) was much stronger than the simple harmonic response to the 20 Hz single-eye stimulus (indicating a constructive interaction between the interleaved dichoptic stimuli), and the response at 20 Hz to the interleaved stimulus (middle) was weaker than the response to the 20 Hz single-eye stimulus (indicating some interference between the interleaved dichoptic stimuli at 20 Hz). These results were achieved both on an individual basis (as shown in FIG. 6) and across a collective number of patients (as shown in FIG. 7). As such, it has been observed that a 20 Hz interleaved stimulus produces a stronger stimulation response as compared to a 40 Hz stimulus.

Figure 8A:
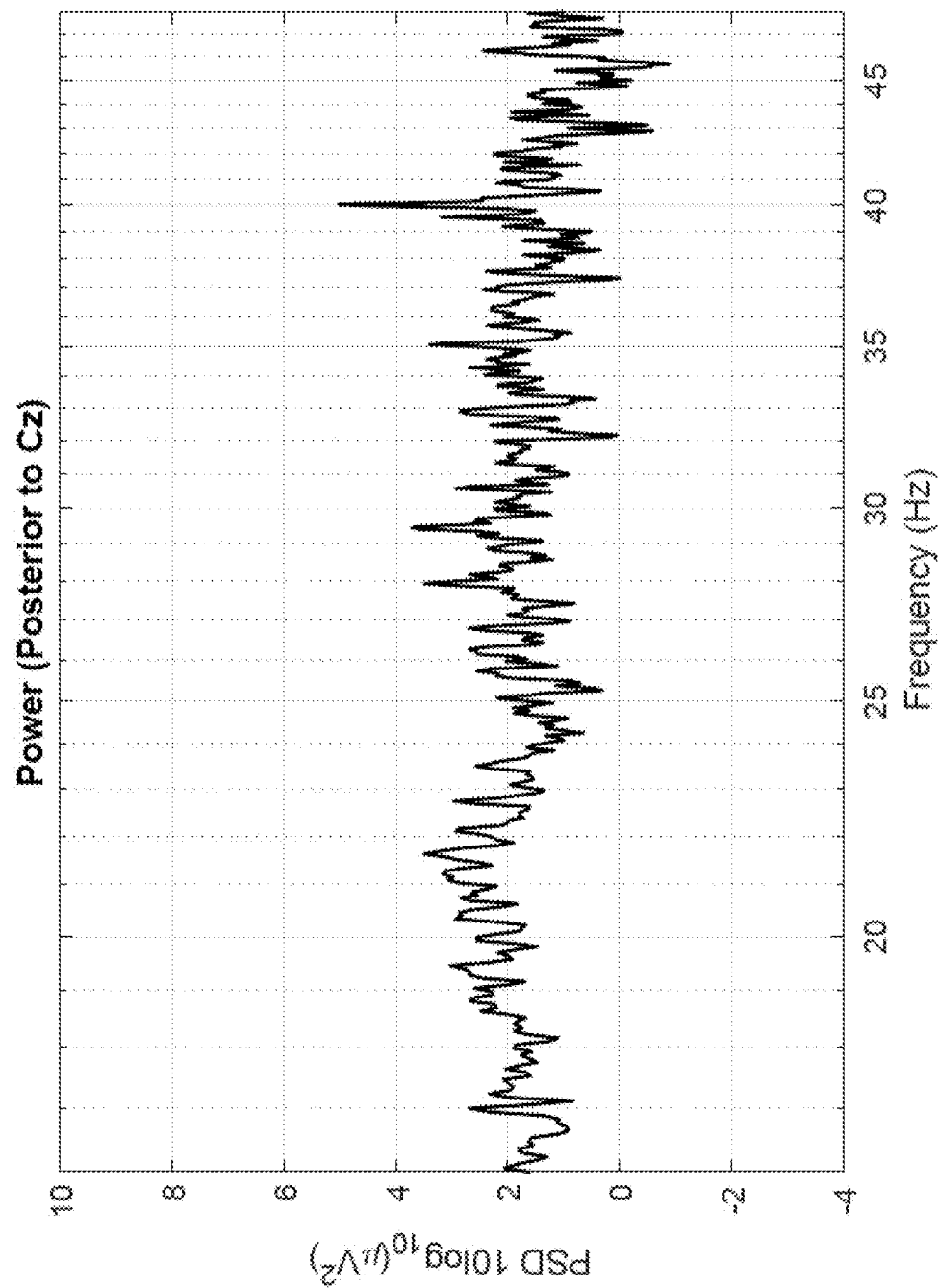
Figure 8C:
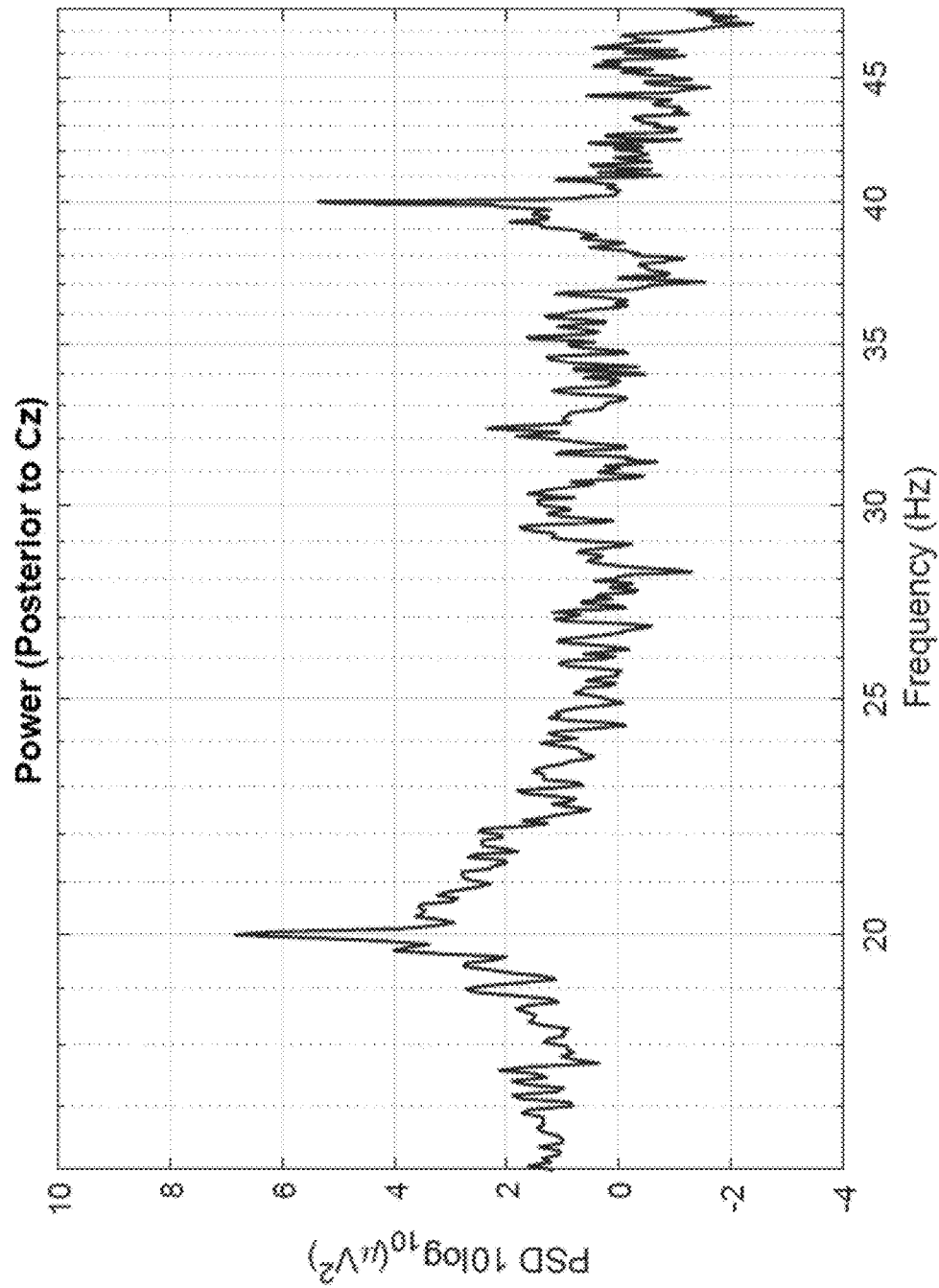
Figure 8D:
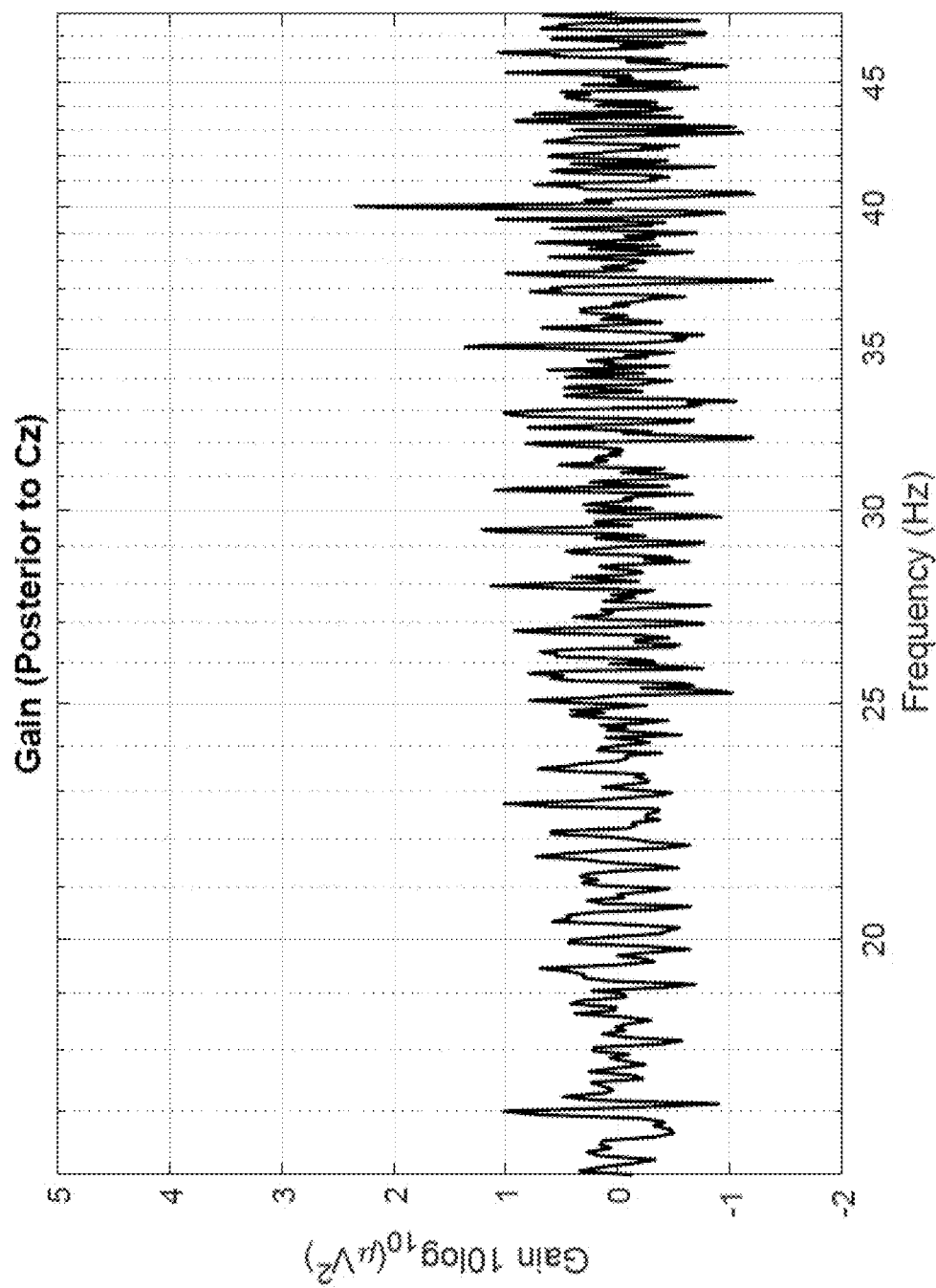
Figure 8E:
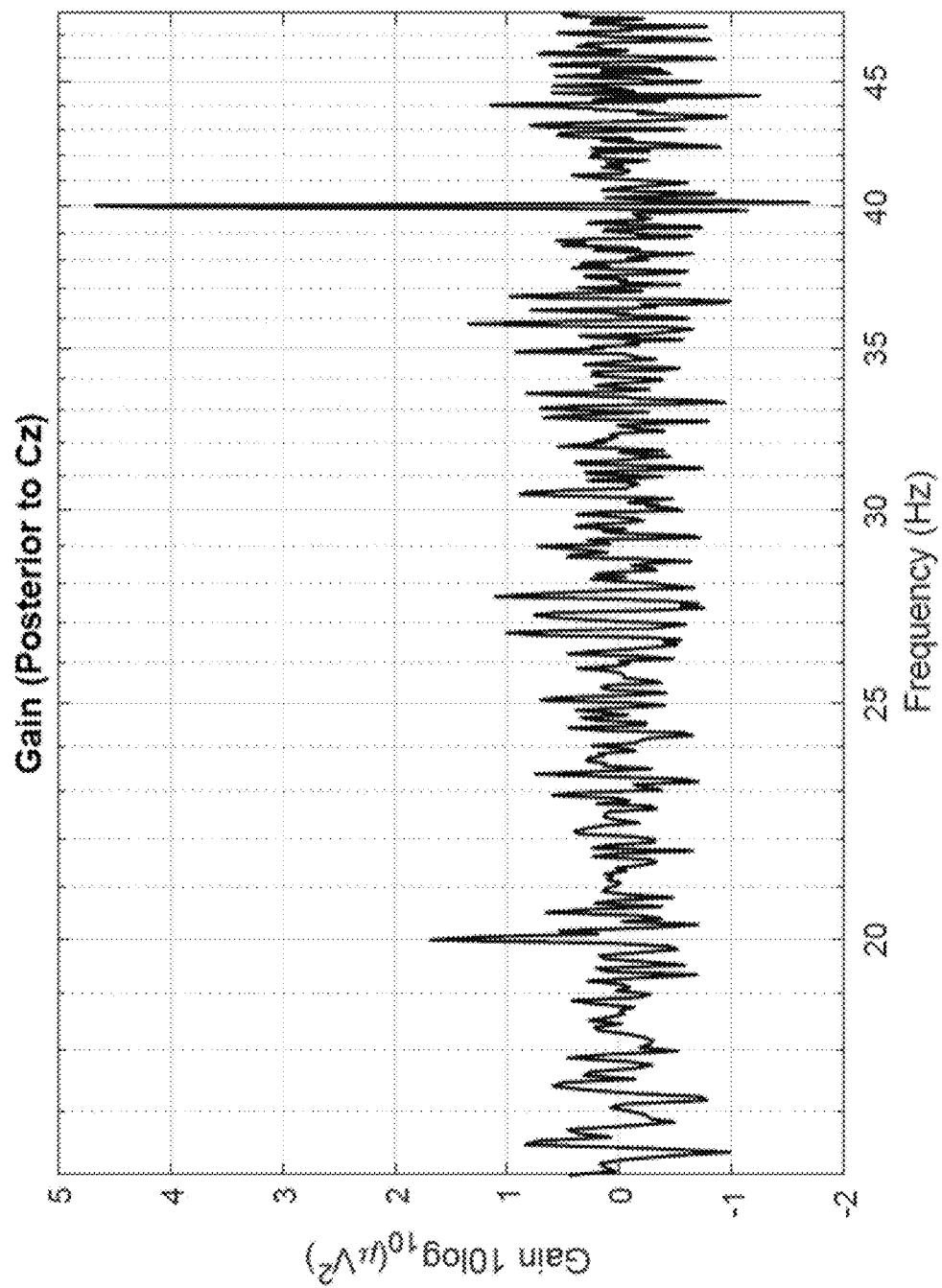
Figure 8F:
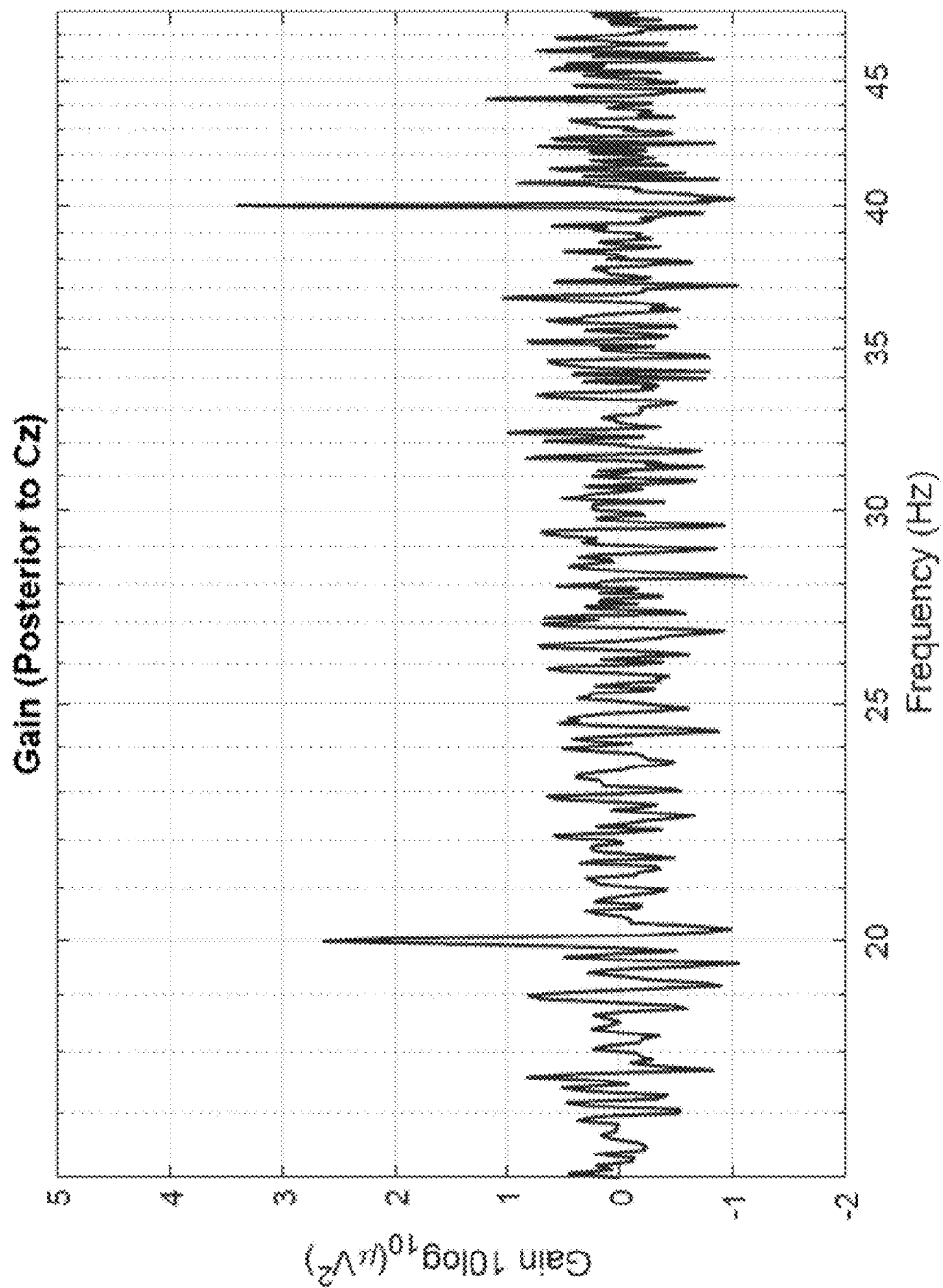

Referring now to FIGS. 8A-8F, depicted are a series of graphs illustrating a power spectral density and gain for the different types of input stimulus shown and described above with reference to FIG. 6 and FIG. 7. The graphs show log power (in dB, e.g., $10 \log_{10} (\mu V^2)$) and gain (relative to the local mean), averaged over subjects, for electrodes posterior to the Cz electrode, where the strongest responses to visual stimuli are expected to occur. Specifically, FIG. 8A-FIG. 8C illustrate graphs of a power spectral density of stimulation responses, in response to input stimuli at 40 Hz (both eyes), 20 Hz interleaved (dichoptic), 20 Hz to one eye, respectively. FIG. 8D-FIG. 8F illustrate graphs of a gain of stimulation responses, in response to the same respective input stimuli as those shown in FIG. 8A-FIG. 8C. As shown in FIG. 8B and FIG. 8E, 20 Hz interleaved produces the strongest stimulation response (both as measured by log power and gain) at 40 Hz, when compared to the other input stimuli, but a weaker response at 20 Hz compared to the single-eye stimulus. Additionally, in comparison to the 40 Hz stimulus applied to both eyes, the 20 Hz interleaved (dichoptic stimulus) has approximately 4 dB greater power in the response than the 40 Hz stimulus (as shown in FIG. 8B as compared to FIG. 8A) and approximately 2.5 dB greater gain than the 40 Hz stimulus (as shown in FIG. 8F as compared to FIG. 8E). As such, interleaving stimulus has been shown to produce stronger stimulation responses at a target frequency than supplying visual stimulus at the target frequency itself.

Figure 9:
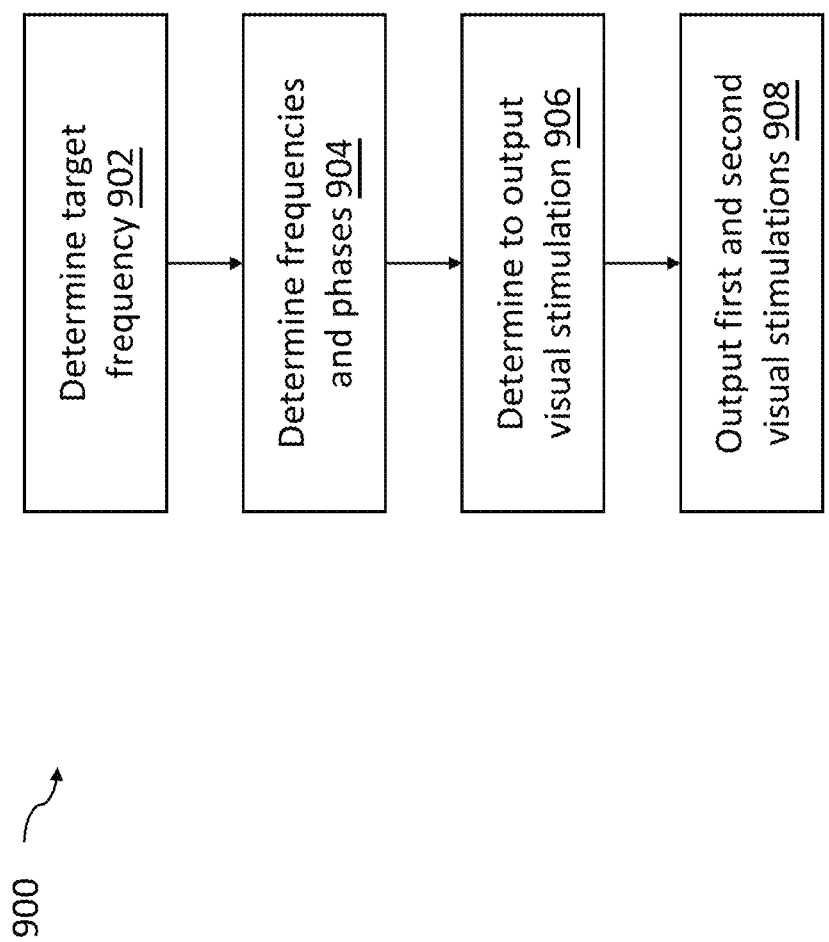
FIG. 9 is a flowchart showing an example method of providing counterphased binocular stimulation, according to an example implementation of the present disclosure.

Referring now to FIG. 9, depicted is a flowchart showing an example method 900 of providing counterphased binocular or dichoptic stimulation, according to an example implementation of the present disclosure. The method 900 may be performed and/or implemented by the components, elements, and/or hardware described herein, such as those described above with reference to FIG. 1-FIG. 8F. As a brief overview, at 902, a device may determine a target frequency. At 904, the device may determine frequencies and phases. At 906, the device may determine to output visual stimulation. At 908, the device may output first and second visual stimulations.

At 902, a device may determine a target frequency. The device may be or include the control system 102 (of FIG. 1) including, for example, the OSM 108. The device may determine the target frequency based on or according to various received, detected, and/or identified inputs. For example, the device may determine the target frequency responsive to receiving a user-input (e.g., from a patient, from a treating professional, etc.) via an input/output device. As another example, the device may determine the target frequency responsive to identifying the target frequency in a treatment schedule of a patient profile (e.g., maintained by the profile manager 1306). As yet another example, the device may determine the target frequency based on feedback from a simulation (e.g., via the entrainment simulator 1308). The target frequency may be a frequency in which stimulation of the patient's brain is to be received. As such, the target frequency may not be a frequency of visual stimulation, but rather a frequency of a stimulation response.

At 904, the device may determine frequencies and phases. In some embodiments, the device may determine, derive, compute, or otherwise identify frequency and phases for visual stimulation, to achieve, produce, solicit, or otherwise provide the frequency response at the target frequency. In some embodiments, the device may determine an oscillation state for each eye of the patient, where the oscillation state includes a frequency and phase of oscillation for visual stimulation. The oscillation state of each eye may together provide the frequency response at the target frequency. In other words, the oscillation state (e.g., including a first frequency and first phase) for a first eye (e.g., the left eye) and the oscillation state (e.g., including a second frequency and second phase) for a second eye (e.g., the right eye) may together provide the frequency response in the patient's brain at the target frequency.

In some embodiments, the device may determine the oscillation states based on or according to the target frequency. For example, the device may determine the frequency for the oscillation states as a function of the target frequency. In some embodiments, a sum of the first and second frequencies (e.g., of the respective oscillation states) may be equal to the target frequency. For example, the first frequency may be equal to half of the target frequency, and the second frequency may be equal to half of the target frequency. Additionally, the phases for the respective oscillation states may be counterphased to one another (e.g., the oscillation states may be out of phase). In other words, the first phase and the second phase (e.g., of the respective oscillation states) may be opposite to one another.

In one example, the target frequency determined at 902 may be equal to between 35 and 40 Hz. For instance, the target frequency may be determined to be 38 Hz. The device may determine the first and second frequency and the first and second phases according to the target frequency. For example, the device may determine the first phase to be opposite/counterphased/anti-phased to the second phase, such that the resultant visual stimulation produces a constructive effect. The device may determine the first and second frequency to be equal to half of the target frequency, such that the resultant visual stimulation (when combined) produces a stimulation response at the target frequency. Continuing the above example, the device may determine the first frequency and the second frequency to be equal to one another, and between 17.5 and 20 Hz (e.g., 19 Hz).

At 906, the device may determine to output visual stimulation. In some embodiments, the device may determine to output visual stimulation to produce a stimulation response at the target frequency. The device may determine to output the visual stimulation responsive to determining the frequency and phases which together produce the stimulation response at the target frequency. The device may determine to output the visual stimulation according to a schedule (e.g., a therapeutic schedule of a session). The device may determine to output the visual stimulation responsive to receiving a signal (e.g., from an input device) to commence visual stimulation of a patient.

At 908, the device may output first and second visual stimulations. In some embodiments, the device may output a first visual stimulation at a first frequency and phase to a first eye, and a second visual stimulation at a second frequency and phase to a second eye. The first visual stimulation may include or correspond to the first oscillation state and the second visual stimulation may include or correspond to the second oscillation state. In other words, the first visual stimulation may have the first frequency and phase and the second visual stimulation may have the second frequency and phase, both of which described above with reference to 904. The first and second visual stimulation may together provide the stimulation response at the target frequency. In other words, the first and second frequency may not be the same as the target frequency. However, because the first and second visual stimulation are constructive (due to the first phase and second phase being anti-phased to or interleaved with one another), the first visual stimulation and the second visual stimulation may together provide the stimulation response at the target frequency.

In some embodiments, the device may output the first and second visual stimulations by controlling one or more light sources (e.g., light sources 104) to output light at the first and second frequency and first and second phases. For example, the device may communicate a signal (e.g., either via a wired or wireless connection) to the light source(s) 104 to output the visual stimulation. The device may communicate first signal(s) to a first set of light source(s) 104 (e.g., first light source(s) 104(1)) to output the first visual stimulation to one eye of the patient, and communicate second signal(s) to a second set of light source(s) 104 (e.g., second light source(s) 104(2)) to output the second visual stimulation to another eye of the patient.

In some embodiments, the device which performs 902-908 may include the lights which output the visual stimulation. For example, the device may include the light sources 104 described above with reference to FIG. 1. For instance, the device may include the head-wearable device 300 and/or the system 400. In some embodiments, the device which performs 902-908 may not include the lights. For example, the device may be communicably coupled to the light sources 104, and output the first and second visual stimulation by sending/communicating/transmitting signals which cause the light sources 104 to output the visual stimulation.

In some embodiments, the device may output an audio signal while outputting the first and second visual stimulation. The audio signal may be synchronized to the first and second visual stimulation, as described above. In some embodiments, the audio signal may be or correspond to music. The device may output the audio signal by transmitting the audio signal to an audio output device, to output the music. The device may modify the audio signal and/or coordinate the first and second visual stimulation, such that the first and second visual stimulation are synchronized with the music corresponding to the audio signal.

Figure 10:
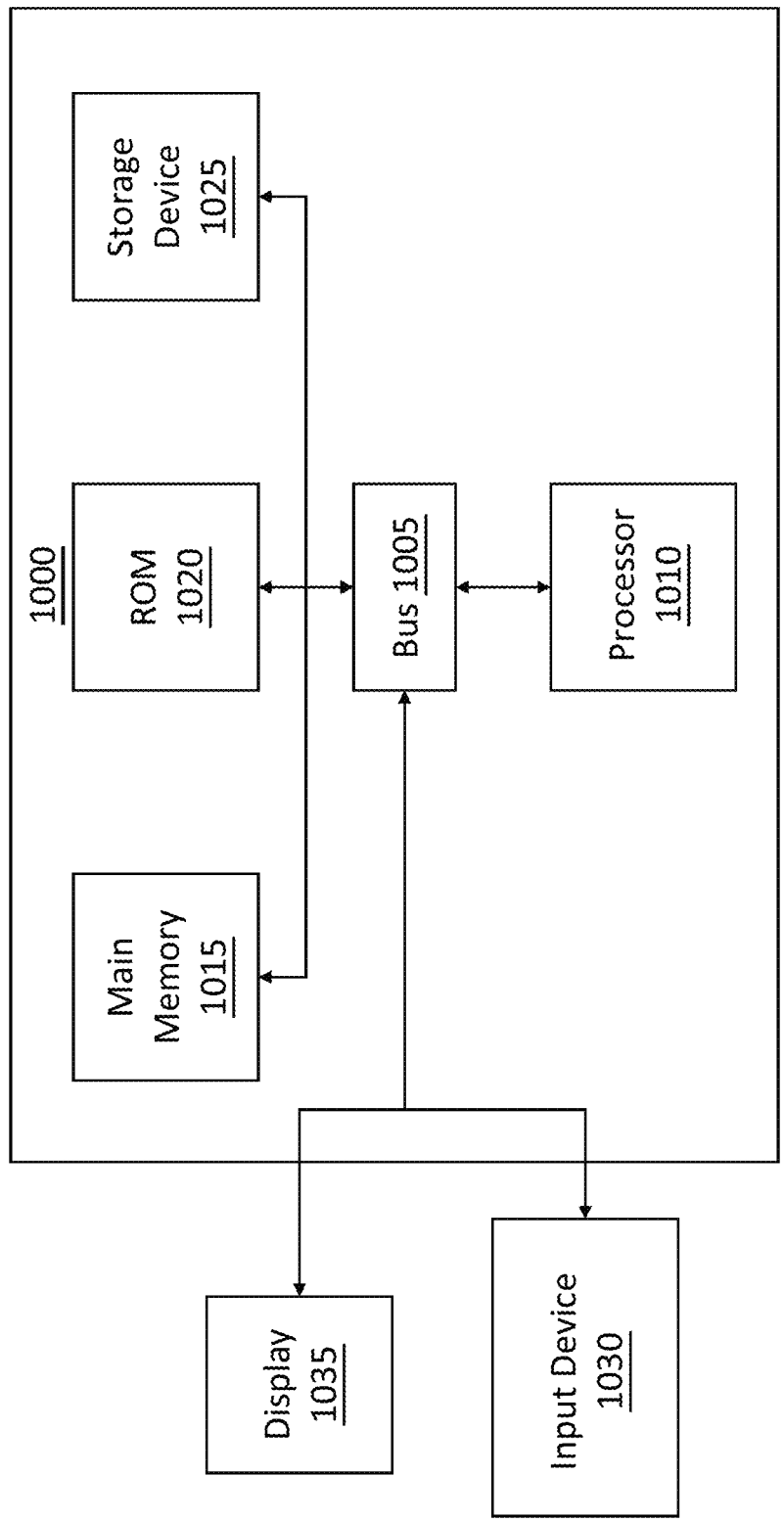
FIG. 10 is a block diagram of an example computer system, according to an example implementation of the present disclosure.

FIG. 10 depicts an example block diagram of an example computer system 1000. Various components, elements, and/or hardware described herein (such as those described with reference to FIG. 1) may be implemented by, via, and/or on the computer system 1000 including components thereof. The computer system or computing device 1000 can include or be used to implement a data processing system or its components. The computing system 1000 includes at least one bus 1005 or other communication component for communicating information and at least one processor 1010 or processing circuit coupled to the bus 1005 for processing information. The computing system 1000 can also include one or more processors 1010 or processing circuits coupled to the bus for processing information. The computing system 1000 also includes at least one main memory 1015, such as a random access memory (RAM) or other dynamic storage device, coupled to the bus 1005 for storing information, and instructions to be executed by the processor 1010. The main memory 1015 can be used for storing information during execution of instructions by the processor 1010. The computing system 1000 may further include at least one read only memory (ROM) 1020 or other static storage device coupled to the bus 1005 for storing static information and instructions for the processor 1010. A storage device 1025, such as a solid state device, magnetic disk or optical disk, can be coupled to the bus 1005 to persistently store information and instructions.

The computing system 1000 may be coupled via the bus 1005 to a display 1035, such as a liquid crystal display, or active matrix display, for displaying information to a user. An input device 1030, such as a keyboard or voice interface may be coupled to the bus 1005 for communicating information and commands to the processor 1010. The input device 1030 can include a touch screen display 1035. The input device 1030 can also include a cursor control, such as a mouse, a trackball, or cursor direction keys, for communicating direction information and command selections to the processor 1010 and for controlling cursor movement on the display 1035.

The processes, systems and methods described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. Hard-wired circuitry can be used in place of or in combination with software instructions together with the systems and methods described herein. Systems and methods described herein are not limited to any specific combination of hardware circuitry and software.

Although an example computing system has been described in FIG. 10, the subject matter including the operations described in this specification can be implemented in other types of digital electronic circuitry, or in computer software, firmware, or hardware, including the structures disclosed in this specification and their structural equivalents, or in combinations of one or more of them.

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Systems and methods described herein may be embodied in other specific forms without departing from the characteristics thereof. References to any terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

What is claimed is:

1. A method comprising:
   identifying, by one or more processors, a target frequency of a stimulation response;
   determining, by the one or more processors, according to the target frequency, a first frequency for stimulation to a first eye and a second frequency for stimulation to a second eye, the target frequency being different than and harmonically related to the first frequency and the second frequency, the first frequency being counterphased with respect to the second frequency; and
   transmit, by the one or more processors, one or more signals to one or more output devices, to provide stimulation to the first eye and the second eye, the stimulation simultaneously output at the first frequency to the first eye and the second frequency to the second eye, to produce the stimulation response at the target frequency.

2. The method of claim 1, wherein the first frequency and the second frequency are substantially half of the target frequency.

3. The method of claim 1, wherein the stimulation output to the first eye and to the second eye comprises visual stimulation output to the first eye and the second eye.

4. The method of claim 1, wherein the target frequency is equal to 38 Hz, the first frequency is equal to 19 Hz, and the second frequency is equal to 19 Hz.

5. The method of claim 1, wherein the one or more output devices comprises one or more first light sources and one or more second light sources, the method further comprising:
   transmitting, by the one or more processors, a first signal of the one or more signals to the one or more first light sources to output light at the first frequency, and
   transmitting, by the one or more processors, a first signal of the one or more signals to the one or more second light sources to output light at the second frequency.

6. The method of claim 5, wherein the one or more first light sources are located at a first position of a head-wearable device and the one or more second light sources located at a second position of the head-wearable device, the first position corresponding to stimulating the first eye when the head-wearable device is worn, and the second position corresponding to stimulating the second eye when the head-wearable device is worn.

7. The method of claim 1, wherein the one or more output devices comprise an audio output device and one or more light sources, the method further comprising:
   transmitting, by the one or more processors to the audio output device, an audio signal for outputting while the stimulation is provided via the one or more light sources to the first eye and the second eye.

8. The method of claim 1, wherein the target frequency is in a frequency band, the frequency band being greater than 40 Hz, between 30 Hz and 40 Hz, between 13 Hz and 30 Hz, between 8 Hz and 13 Hz, between 4 Hz and 8 Hz, or between 0.5 Hz and 4 Hz.

9. The method of claim 1, wherein determining the first frequency and the second frequency comprises determining, by the one or more processors, a first oscillation state for the first eye and a second oscillation state for the second eye, the first oscillation state comprising the first frequency and the second oscillation state comprising the second frequency.

10. A system comprising:
    one or more output devices; and
    one or more processors configured to:
      identify a target frequency of a stimulation response;
      determine, according to the target frequency, a first frequency for stimulation to a first eye and a second frequency for stimulation to a second eye, the target frequency being different than and harmonically related to the first frequency and the second frequency, the first frequency being counterphased with respect to the second frequency; and
      transmit one or more signals to the one or more output devices, to provide stimulation to the first eye and the second eye, the stimulation simultaneously output at the first frequency to the first eye and the second frequency to the second eye, to produce the stimulation response at the target frequency.

11. The system of claim 10, wherein the first frequency and the second frequency are substantially half of the target frequency.

12. The system of claim 10, wherein the target frequency is equal to 38 Hz, the first frequency is equal to 19 Hz, and the second frequency is equal to 19 Hz.

13. The system of claim 10, wherein the one or more output devices comprises one or more first light sources and one or more second light sources, wherein the one or more processors are configured to:
    transmit a first signal of the one or more signals to the one or more first light sources to output light at the first frequency, and
    transmit a first signal of the one or more signals to the one or more second light sources to output light at the second frequency.

14. The system of claim 13, wherein the one or more first light sources are located at a first position of a head-wearable device and the one or more second light sources located at a second position of the head-wearable device, the first position corresponding to stimulating the first eye when the head-wearable device is worn, and the second position corresponding to stimulating the second eye when the head-wearable device is worn.

15. The system of claim 10, wherein the one or more output devices comprise an audio output device and one or more light sources, wherein the one or more processors are configured to:

transmit, to the audio output device, an audio signal for outputting while the stimulation is provided via the one or more light sources to the first eye and the second eye.

16. The system of claim 10, wherein the target frequency is in a frequency band, the frequency band being greater than 40 Hz, between 30 Hz and 40 Hz, between 13 Hz and 30 Hz, between 8 Hz and 13 Hz, between 4 Hz and 8 Hz, or between 0.5 Hz and 4 Hz.

17. The system of claim 10, wherein to determine the first frequency and the second frequency, the one or more processors are configured to determine a first oscillation state for the first eye and a second oscillation state for the second eye, the first oscillation state comprising the first frequency and the second oscillation state comprising the second frequency.

18. A device comprising:
one or more output devices; and
one or more processors configured to:
identify a target frequency of a stimulation response;
determine, according to the target frequency, a first frequency for stimulation to a first eye and a second frequency for stimulation to a second eye, the target frequency being different than and harmonically related to the first frequency and the second frequency, the first frequency being counterphased with respect to the second frequency; and
transmit one or more signals to the one or more output devices, to provide stimulation to the first eye and the second eye, the stimulation simultaneously output at the first frequency to the first eye and the second frequency to the second eye, to produce the stimulation response at the target frequency.

* * * * *